United States Patent [19]

Cauwet et al.

[11] Patent Number: 5,478,562
[45] Date of Patent: Dec. 26, 1995

[54] COSMETIC COMPOSITION CONTAINING AT LEAST ONE SURFACE-ACTIVE AGENT OF THE ALKYL POLYGLYCOSIDE AND/OR POLYGLYCEROLATED TYPE AND AT LEAST ONE POLYETHERURETHANE

[75] Inventors: Daniele Cauwet, Paris; Claude Dubief, Le Chesnay, both of France

[73] Assignee: L'Oreal, Paris, France

[21] Appl. No.: 270,324

[22] Filed: Jul. 5, 1994

Related U.S. Application Data

[63] Continuation of Ser. No. 14,989, Feb. 8, 1993, abandoned.

[30] Foreign Application Priority Data

Feb. 7, 1992 [FR] France ................... 92 01419

[51] Int. Cl.$^6$ ............ A61K 7/075; A61K 9/107; A61K 7/06
[52] U.S. Cl. ............ 424/401; 424/70.11; 424/70.31; 424/DIG. 1; 424/73; 424/70.2; 424/70.6; 424/DIG. 3; 424/47; 424/486; 252/DIG. 5; 252/DIG. 13; 514/944; 514/844; 514/845; 514/846; 514/937; 514/941
[58] Field of Search ............ 424/401, 70, 71, 424/47, DIG. 1, 73, 486, 78.02, 78.39, 78.38, 70.11, 70.31; 252/352, 357, DIG. 1, DIG. 5, DIG. 13; 514/54, 844–846, 937, 941, 944

[56] References Cited

U.S. PATENT DOCUMENTS

| | | | |
|---|---|---|---|
| 3,578,719 | 5/1971 | Kalopissis et al. | 260/611 |
| 3,666,671 | 5/1972 | Kalopissis et al. | 252/173 |
| 3,877,955 | 4/1975 | Kalopissis et al. | 106/266 |
| 4,155,892 | 5/1979 | Emmons et al. | 524/507 |
| 4,307,079 | 12/1981 | Zorayan et al. | 424/70 |
| 4,963,535 | 10/1990 | Sebag et al. | 424/70 |
| 5,167,281 | 12/1992 | Kalfoglou | 252/8.554 |

FOREIGN PATENT DOCUMENTS

| | | |
|---|---|---|
| 0260430 | 3/1988 | European Pat. Off. . |
| 2128627 | 5/1984 | United Kingdom . |

OTHER PUBLICATIONS

Dapral T210 et T212 "Epaississants ajustables", AKZO.

*Primary Examiner*—Edward J. Webman
*Attorney, Agent, or Firm*—Jacobson, Price, Holman & Stern

[57] ABSTRACT

The invention relates to a cosmetic composition containing in a cosmetically acceptable medium at least one nonionic surface-active agent of the family of alkyl polyglycosides and/or a polyglycerolated nonionic surface-active agent and at least one polyetherurethane, as well as a process for cosmetic treatment consisting in applying to the skin or the hair a cosmetically effective amount of this composition.

27 Claims, No Drawings

COSMETIC COMPOSITION CONTAINING AT LEAST ONE SURFACE-ACTIVE AGENT OF THE ALKYL POLYGLYCOSIDE AND/OR POLYGLYCEROLATED TYPE AND AT LEAST ONE POLYETHERURETHANE

This application is a continuation of application Ser. No. 08/014,989, filed Feb. 8, 1993, abandoned.

The invention relates to cosmetic compositions containing at least one nonionic surface-active agent of the alkyl polyglycoside and/or polyglycerolated type and at least one polyetherurethane.

U.S. Pat. No. 4,155,892 essentially describes the use of some polyetherurethanes for thickening latex-based paint compositions.

Polyetherurethanes are moreover known as thickeners for compositions containing surface-active agents. Europena Application EP 260 430 describes polyetherurethanes capable of being used in cosmetics for thickening oxyethylenated fatty alcohols containing 8.5 to 15 moles of ethylene oxide, and oxyethylenated sorbitan monoester containing 20 moles of ethylene oxide.

Surface-active agents of the family of alkyl polyglycosides or polyglycerolated agents have already been recommended in washing compositions for the hair or the skin. They are mild detergents which are well tolerated and are biodegradable.

Hair which is attacked by environmental agents such as light or chemical treatments, and washed with conventional washing bases, is difficult to disentangle and this disadvantage is increased further in the case of fine hair. The compositions, containing polyetherurethanes and nonionic surface-active agents, described in European Application EP 260 430 do not confer disentangling properties.

The applicant has just discovered, surprisingly, that the combination, in washing and/or treating compositions for keratinous materials, of polyetherurethanes with special nonionic surface-active agents of the alkyl polyglycoside and/or polyglycerolated type conferred on these compositions substantially improved disentangling properties. Moreover, the combination conforming to the invention makes it possible to obtain a very mild foam compared with the generally harsh foam resulting from the use of nonionic agents.

Furthermore, the applicant observed that compositions containing such a combination had good cosmetic properties such as mildness and a pleasant feel.

The subject of the present invention is therefore cosmetic compositions containing at least one nonionic surface-active agent of the alkyl polyglycoside and/or polyglycerolated type and at least one polyetherurethane.

Another subject of the invention consists in the use of these compositions for treating and/or washing keratinous materials such as the hair or the skin, hair being particularly preferred.

Another subject of the invention consists in a process for the cosmetic treatment of the hair or the skin by means of the compositions conforming to the invention; the process for washing and treating hair being particularly preferred.

Other subjects of the invention will emerge on reading the following description and examples.

The cosmetic compositions according to the invention contain, in a cosmetically acceptable medium, at least one nonionic surface-active agent of the alkyl polyglycoside and/or polyglycerolated type and at least one polyetherurethane.

Among the polyetherurethanes which may be used according to the invention, there may be mentioned those of the following formula (I):

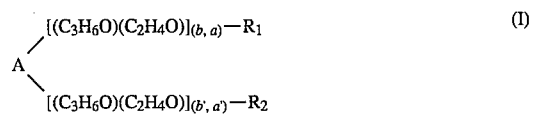

in which, $[(C_3H_6O)(C_2H_4O)]_{(b_i, a_i)}$, with $(b_i, a_i)$ denoting $(b, a)$ or $(b', a')$, means that is a random polymer of propylene oxide and ethylene oxide containing a mole of ethylene oxide and a mole of propylene oxide distributed in a random manner in the polymeric chain, A denotes a divalent radical derived from an aliphatic, cycloalophatic or aromatic diisocyanate, preferably a divalent radical derived from a polyethylene diisocyanate, tolylene diisocyanate or methanediphenylene diisocyanate; $R_1$ and $R_2$, which are identical or different, denote a $C_8$–$C_{30}$, preferably $C_{10}$–$C_{20}$, and more particularly $C_{12}$–$C_{18}$ alkyl or alkenyl radical;

$a_i$ and $b_i$, which are identical or different, being such that the sum of $a_i + b_i$ ranges from 20 to 200 moles, and preferably from 60 to 120 moles;

the molar ratio $a_i/b_i$ is between 30/70 and 90/10, preferably between 50/50 and 90/10 and more particularly between 70/30 and 85/15.

The compounds of the formula (I) which are more particularly preferred are those where A denotes the hexamethylene diisocyanate residue; $R_1$ and $R_2$ denote a lauryl radical or a mixture of radicals derived from tallow; the radicals $R_i$—$[(C_2H_4)—(C_3H_6O)]_{(a_i, b_i)}$ preferably have a molecular weight of the order of 4000, with $R_i$ denoting $R_1$ or $R_2$ and $a_i$ and $b_i$ denoting a and b or a' and b' as defined above.

The compounds of the formula (I) can be obtained by reaction of a diisocyanate with one or two polyoxyethylenated and polyoxypropylenated fatty alcohols of formula $R_i[(OC_2H_4)—(OC_3H_6)]_{(a_i, b_i)}$ OH in which $R_i$, $a_i$ and $b_i$ denote $R_1$ or $R_2$, a or a' and b or b' which have the meanings given above, which is(are) used in excess relative to the diisocyanate so that the latter is completely consumed.

Compounds of the formula (I) which may be used according to the invention are described in European Application EP 260 430 and marketed under the DAPRAL T210 and DAPRAL T212 by AKZO.

Other polyetherurethanes which may be used according to the invention possess at least three urethane groups. Among them, there may be mentioned those belonging to one of the following three groups of polyetherurethanes:

Group I

The polyetherurethanes of the following formula:

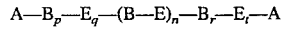

in which, n is a number between 1 and 10, p, q, r and t, independently of each other, are equal to either 0 or 1, with at least one of q or r being equal to 1, and t being equal to zero when r is equal to 0, provided that when q is equal to 1, then either p, r and t are equal to 0, or p is equal to 0 and r and t are equal to 1, or t is equal to 0 and r and p are equal to 1, and when q is equal to 0, then r is equal to 1 and p and t are equal to 0;

Group II

The polyetherurethanes of the following formula II

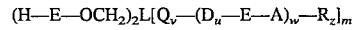

in which, m is an integer ranging from 2 to 4 and s is an integer ranging from 0 to 2, the sum of m and s ranging from 2 to 4, w is an integer ranging from 1 to 3, and each of u, v and z is, independently of each other, 0 or 1; L represents X, Y or —O—, X being a hydrophobic hydrocarbon radical containing at least one carbon atoms, and preferably one to four carbon atoms, and Y a trivalent hydrophobic radical chosen from the following groups:

—OCONH(CH$_2$)$_6$N[CONH(CH$_2$)$_6$NHCO—O—]$_2$, CH$_3$C[CH$_2$O—OCNHC$_7$H$_6$NHCO—]$_3$ and CH$_3$CH$_2$C[CH$_2$O—OCNHC$_7$H$_6$NHCO—]$_3$ and CH$_3$CH$_2$C[CH$_2$O—OCNHC$_7$H$_6$NHCO—]$_3$;

Q represents the group —CH$_2$C—, and D the group —CH$_2$O—, provided that, a) when L represents X, then u and w are each equal to 1, v and z are equal to 0, m is equal to not less than 2 and the sum of m and s is 4;

b) when L represents Y, then u, v and s are each equal to 0, m is equal to 3, w is 2 or 3 and z is 0 or 1; and c) when L represents —O—, then v and u are each equal to 1, w ranges from 1 to 3, m is equal to 2, and s and z are each equal to 0;

in each of the formulae for both of these groups, A and R represent a hydrophobic organic radical; B a hydrophobic divalent group of formula:

$$-\overset{O}{\underset{\|}{C}}NH-G-NH\overset{O}{\underset{\|}{C}}-O-,$$

in which G is a divalent radical derived from an organic di- or triisocyanate all of whose isocyanate groups have reacted; and E represents a nonionic, divalent hydrophilic polyether group.

Group III

The polyetherurethanes are obtained by reaction (a) of a polyfunctional reagent chosen from organic polyols having at least three hydroxyl groups, organic polyisocyanates having at least three isocyanate groups, and mixtures thereof;

(b) a difunctional reagent chosen from organic diols, organic diisocyanates, and mixtures thereof, the diol being present in the reaction mixture when a polyisocyanate is present and the diisocyanate being present when the polyol is present;

(c) a hydroxyl or amino monofunctional compound in a quantity sufficient to trap any isocyanate group which did not react during the reaction between (a) and (b), and to prevent coagulation of the reaction mixture; and, optionally, (d) an organic monoisocyanate for trapping the hydroxyl groups remaining after reaction between (a) and (b); a reaction in which at least either the polyol or the diol contains at least one water-soluble polyether segment with a molecular weight of not less than 1500, the sum of the carbon atoms in the reagents containing isocyanate groups, hydroxyl groups and amino groups is not less than 20, and the average molecular weight of the components of the composition is about 10,000 to 200,000.

The compounds of groups I, II and III which may be used according to the invention are described in more detail in U.S. Pat. No. 4,155,892, and are marketed under the name ACRYSOL by the company ROHM and HAAS.

The alkyl polyglycosides which may be used in conformity with the invention are in particular of the following formula (II):

$$R(C_6H_{10}O_5)_x-H \quad (II)$$

which corresponds to the structural formula (III)

(III)

[structure of alkyl polyglycoside showing R—O— attached to a pyranose ring with OH, OH, OH, and CH$_2$—O—H groups, with subscript x]

in which,

R denotes an alkyl or alkenyl radical or a mixture of alkyl or alkenyl radicals containing a linear or branched C$_8$–C$_{24}$ chain;

x is a number between 1 and 15.

The alkyl polyglycoside compounds with the structural formula (III) defined above, used in conformity with the invention, are preferably represented by the products sold by the company HENKEL under the name APG, such as the products APG 300, APG 350, APG 500, APG 550, APG 625 and APG base 10–12; the products sold by the company SEPPIC under the names TRITON CG 110 (or ORAMIX CG 110) and TRITON CG 312 (or ORAMIX NS 10); those sold by the company BASF under the name LUTENSOL GD 70.

The nonionic surface-active agents of the polyglycerolated type which are used in conformity with the present invention, are preferably chosen from the following polyhydroxypropyl ether compounds:

(A) The compounds of the formula (IV):

$$RO[(C_3H_5(OH)—]_nH \quad (IV)$$

in which the group [C$_3$H$_5$(OH)] represents the following structures taken together or separately $$[CH_2CHOH—CH_2—O—] \quad (IVa)$$

$$+CH_2—\underset{\underset{CH_2OH}{|}}{CH}—O+ \quad (IVb)$$

and $$+CH—CH_2—O+ \quad (IVc)$$
$$\phantom{+}|$$
$$CH_2OH$$

and R and n have one of the meanings below:

a) R represents a C$_{10}$–C$_{14}$ alkyl radical or a mixture of C$_{10}$–C$_{14}$ alkyl radicals and n is an integer or a decimal from 2 to 10, preferably 3 to 6.

b) R represents a residue:

$$R_2CONHCH_2—CH_2—CH_2OCH_2—CH_2— \quad (V)$$

where R$_2$ denotes a C$_{11}$–C$_{17}$ alkyl and/or alkenyl radical or a mixture of C$_{11}$–C$_{17}$ alkyl and/or alkenyl radicals and n denotes an integer or a decimal from 1 to 5, and preferably from 1.5 to 4.

c) R represents a residue:

$$R_3—CHOH—CH_2— \quad (VI)$$

where R$_3$ denotes an aliphatic, cycloaliphatic or arylaliphatic C$_7$–C$_{21}$ radical and mixtures thereof, the aliphatic chains denoting in particular alkyl chains which may contain from 1 to 6 ether, thioether and/or hydroxymethylene groups and n denotes an integer or decimal from 1 to 10.

These surface-active agents of formula (IV) may be prepared according to the procedures described in Patents FR 1,477,048; 2,328,763 and 2,091,516;

(B) The compounds prepared by condensation, using acid catalysis, of 2 to 10, preferably 2.5 to 6 moles of glycidol per mole of alcohol or alpha-diol containing 10 to 14 carbon atoms, at a temperature of 50° to 120° C., the glycidol being slowly added to the alcohol or alpha-diol. The process for preparing these compounds is described in Patent FR-A-2 169,787;

(C) The polyhydroxypropyl ether compounds prepared by polyaddition of glycerol monochlorohydrin to a polyhydroxylated organic compound in the presence of a strong base, with constant removal of water by distillation. These compounds are described in French Patent FR-A-2,574,786.

Among the nonionic surface-active agents of the family of polyhydroxypropyl ethers described in paragraphs (A), (B) and (C) above, the preferred compounds are represented by the formulae:

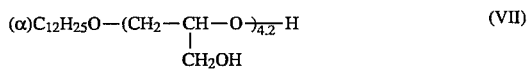

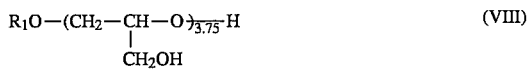

where $R_1$ denotes a mixture of $C_{10}H_{21}$ and $C_{12}H_{25}$ alkyl radicals;

(β) the compounds prepared by condensation, using alkaline catalysis, of 3.5 moles of glycidol with an alpha-diol having 12 carbon atoms, according to the process described in Patent FR-A-2,091,516;

(τ) the compounds of the formula:

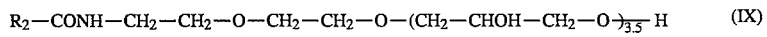

where $R_2$ denotes a mixture of radicals comprising the following alkyl and alkenyl radicals: $C_{11}H_{23}$, $C_{13}H_{27}$, the radicals derived from fatty acids from copra and the radical derived from oleic acid;

(δ) the compounds prepared by condensation of 3.5 moles of glycidol with a mixture of $C_{11}$–$C_{14}$ alpha-diols, described in Patent FR-A-2,091,516.

The polyhydroxypropyl ether nonionic surface-active agent obtained by condensation of glycerol monochlorohydrin (2.5 moles), in the presence of sodium hydroxide, with 1,2-deodecanediol is more particularly preferred.

The polyetherurethanes are used in the compositions conforming to the invention in proportions of between 0.1 and 10% by weight relative to the total weight of the composition, and preferably between 0.3 and 5% by weight.

If the compositions according to the invention are not used for washing keratinous materials, the nonionic surface-active agent(s) of the alkyl polyglycoside and/or polyglycerolated type are used in such compositions in proportions of between 0.5 and 10% by weight relative to the total weight of the composition. These compositions are used especially as compositions to be rinsed off, which are applied after shampooing, dyeing, bleaching, permanent waving or hair straightening.

If the compositions according to the invention are washing compositions, they contain the nonionic surface-active agent(s) in proportions of between 3 and 50% by weight relative to the total weight of the composition, and more particularly between 5 and 30% by weight.

The pH of the compositions conforming to the invention is generally between 2 and 9, more particularly between 3 and 6.

Since the cosmetically acceptable medium, of composition according to the invention, is an aqueous medium, it may be composed of water alone or of a mixture of water and a cosmetically acceptable solvent such as $C_1$–$C_4$ lower alcohols such as ethanol, isopropanol or n-butanol; alkylene glycols such as ethylene glycol, or glycol ethers.

The compositions according to the invention may be provided in the form of liquids which are more or less thickened, gels, emulsions (milks or creams), dilute alcoholic lotions, dispersions, or aerosol foams.

The compositions are for example lotions, milks or emollient creams, lotions, milks or creams for the care of keratinous materials, make-up removing creams or milks, foundations, sun lotions, milks or creams, artificial tanning lotions, milks or creams, shaving creams or foams, aftershave lotions, eye make-up, blushers and foundation for the face, shampoos, bath or shower products, compositions to be rinsed off, to be applied after shampooing, dyeing, bleaching, permanent waving or hair straightening.

The compositions conforming to the invention may optionally contain, in addition, various additives which do not alter the properties of the compositions, such as anionic, cationic, amphoteric or zwitterionic surface-active agents, nonionic surface-active agents other than those described above, anionic, nonionic, cationic or amphoteric polymers, proteins, hydrocarbon-containing oils such as synthetic oils such as isoparaffins or inorganic, vegetable or animal oils, silicone oils, waxes, resins and/or gums, acidifying or alkalinizing agents, preserving agents, active ingredients, other thickeners, suspending agents, emollients, sunscreen agents, perfumes or other adjuvants commonly used in cosmetics.

The compositions conforming to the invention are applied to the skin or the hair in a cosmetically effective amount, depending on the nature of the composition.

A special application of the compositions according to the invention is the application as cosmetic composition for washing and treating keratinous materials, preferably the skin and the hair, and more particularly as shampoo. In this case, the shampoo is applied to wet or dry hair in effective amounts so as to wash them, this application being followed by a rinse.

The following examples are intended to illustrate the invention without, however, being of a restrictive nature.

EXAMPLE 1

A shampoo of the following composition is prepared:

| | |
|---|---|
| Alkyl($C_9$–$C_{10}$–$C_{11}$/20-40-40)polyglycoside (1,4) sold containing 50% AI by the company HENKEL under the name APG 300 | 15 g AI (Active Ingredient) |
| Polyetherurethane sold under the name DAPRAL T210 by the company AKZO | 2.5 g |
| Perfume, preservative qs | |
| Spontaneous pH 6.2 | |
| Water qs | 100 g |

EXAMPLE 2

A shampoo of the following composition is prepared:

| | |
|---|---|
| Alkyl ($C_{10}$–$C_{12}$–$C_{14}$/85-10-5)polyglycoside (1,4) sold containing 55% AI under the name ORAMIX NS 10 by the company SEPPIC | 15 g AI |
| Polyetherurethane sold under the name DAPRAL T212 by the company AKZO | 2 g |
| Perfume, preservative qs | |
| Spontaneous pH 6.2 | |
| Water qs | 100 g |

EXAMPLE 3

A shampoo of the following composition is prepared:

| | |
|---|---|
| Alkyl($C_{10}$–$C_{12}$–$C_{14}$/85-10-5)polyglycoside (1,4) sold containing 55% AI under the name ORAMIX NS 10 by the company SEPPIC | 10 g AI |
| Polyetherurethane sold under the name DAPRAL T210 by the company AKZO | 2 g |
| Surface-active agent of the polyoxyethylenated ether carboxylic acid type of formula: $R(OCH_2CH_2)_nOCH_2COOH$ in which: $R = C_{12}$–$C_{14}$ alkyl chain n = average value of 4.5 sold under the name AKYPO RLM 45 by the Company CHEMY | 5 g AI |
| Diallyl dimethylammonium chloride and acrylamide copolymer sold in aqueous solution containing 8% AI under the name MERQUAT S by the company MERCK | 0.5 g AI |
| Perfume, preservative qs | |
| Spontaneous pH 4.5 | |
| Water | 100 g |

EXAMPLE 4

A shampoo of the following composition is prepared:

| | |
|---|---|
| Polyhydroxypropyl ether nonionic surface-active agent prepared by condensation, using alkaline catalysis, of 3.5 moles of glycidol and a mixture of alpha-diols having 10 to 14 carbon atoms, according to the process described in French Patent No. 2,091,516 | 15 g |
| Polyetherurethane sold under the name DAPRAL T212 by the company AKZO | 2.5 g |
| Perfume, preservative qs | |
| Spontaneous pH 6.8 | |
| Water qs | 100 g |

EXAMPLE 5

A conditioner of the following composition is prepared:

| | |
|---|---|
| Alkyl($C_9$–$C_{10}$–$C_{11}$/20-40-40)polyglycoside (1,4) sold containing 50% AI by the company HENKEL under the name APG 300 | 2 g AI |
| Polyetherurethane sold under the name DAPRAL T210 by the company AKZO | 7 g |
| Cetyltrimethylammonium chloride sold in aqueous solution containing 25% AI under the name DEHYQUART A by the company HENKEL | 1 g AI |
| Preservative qs | |
| Sodium hydroxide qs | pH 6 |
| Water qs | 100 g |

This composition is applied to wet and clean hair. After allowing it to act for a few minutes, the hair is rinsed and dried.

EXAMPLE 6

A shampoo of the following composition is prepared:

| | |
|---|---|
| Alkyl($C_9$–$C_{10}$–$C_{11}$/20-40-40)polyglycoside (1,4) sold containing 50% AI by the company HENKEL under the name APG 300 | 10 g AI |
| Polyetherurethane sold under the name DAPRAL T212 by the company AKZO | 2.5 g |
| Ammonium lauryl sulfate containing 30% AI | 3 g AI |
| Amphoteric polymer derived from chitosan described in French Patent No. 2,137,684 | 1 g |
| Perfume, preservative qs | |
| Spontaneous pH 3.8 | |
| Water qs | 100 g |

EXAMPLE 7

A shampoo of the following composition is prepared:

| | |
|---|---|
| Alkyl($C_9$–$C_{10}$–$C_{11}$/20-40-40)polyglycoside (1,4) sold containing 50% AI by the company HENKEL under the name APG 300 | 15 g AI |
| Polyetherurethane sold in the form of an aqueous dispersion at 20% under the name ACRYSOL RM8 by the company ROHM and HAAS | 5 g AI |
| Perfume, preservative qs | |
| HCl qs | pH 7.3 |
| Water qs | 100 g |

EXAMPLE 8

A shampoo of the following composition is prepared:

| | |
|---|---|
| Alkyl($C_9$–$C_{10}$–$C_{11}$/20-40-40)polyglycoside (1,4) sold containing 50% AI by the company HENKEL under the name APG 300 | 15 g AI |
| Polyetherurethane sold in the form of an aqueous dispersion at 20% under the name ACRYSOL RM2020 by the company ROHM and HAAS | 5 g AI |
| Perfume, preservative qs | |
| HCl qs | pH 6.7 |
| Water qs | 100 g |

EXAMPLE 9

A shampoo of the following composition is prepared:

| | |
|---|---|
| Polyhydroxypropyl ether nonionic surface-active agent prepared by condensation, using alkaline catalysis, of 3.5 moles of glycidol and a mixture of alpha-diols | 10 g |

9

-continued

| | |
|---|---|
| having 10 to 14 carbon atoms, according to the process described in French Patent No. 2,091,516 | |
| Polyetherurethane sold in the form of an aqueous dispersion at 20% under the name ACRYSOL RM8 by the company ROHM and HAAS | 5 g AI |
| Perfume preservative qs | |
| NaOH qs | pH 7 |
| Water qs | 100 g |

EXAMPLE 10

A shampoo of the following composition is prepared:

| | |
|---|---|
| Alkyl[C$_8$–C$_{10}$(50/50)]polyglycoside (2) sold containing 60% AI by the company SEPPIC under the name TRITON CG110 | 48 g AI |
| Polyetherurethane sold in the form of an aqueous dispersion at 20% under the name ACRYSOL RM2020 by the company ROHM and HAAS | 3 g AI |
| Perfume, preservative qs | |
| NaOH qs | pH 7 |
| Water qs | 100 g |

We claim:

1. An aqueous cosmetic composition which contains in a cosmetically acceptable medium 0.5 to 50% by weight relative to the total weight of the composition of at least one alkyl polyglycoside or polyglycerolated non-ionic surface-active agent and 0.1 to 10% by weight relative to the total weight of the composition of at least one polyetherurethane.

2. The composition as claimed in claim 1, wherein the polyetherurethane is of the following formula:

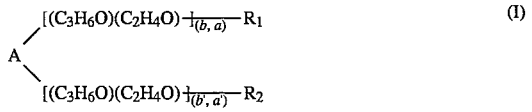

(I)

in which:

$[(C_3H_6O)(C_2H_4O)]_{(b_i, a_i)}$, with $(b_i, a_i)$ denoting $(b, a)$ or $(b', a')$, means that it is a random polymer of propylene oxide and ethylene oxide containing a mole of ethylene oxide and b mole of propylene oxide distributed in a random manner in the polymeric chain, A denotes a divalent radical derived from an aliphatic, cycloaliphatic or aromatic diisocyanate, $R_1$ and $R_2$, which are identical or different, denote a $C_8$–$C_{30}$, alkyl or alkenyl radical;

$a_i$ and $b_i$, which are identical or different, are such that the sum of between $a_i + b_i$ is a number between 20 to 200 moles; the molar ratio $a_i/b_i$ is between 30/70 and 90/10.

3. The composition of claim 2, wherein $R_1$ and $R_2$ denote a $C_{10}$–$C_{20}$ alkyl or alkenyl radical.

4. The composition of claim 2, wherein the sum of between $a_i + b_i$ is a number between 60 to 120 moles.

5. The composition of claim 2, wherein the molar ratio $a_i/b_i$ is between 50/50 and 90/10.

6. The composition as claimed in claim 2, wherein A denotes a divalent radical derived from a polymethylene diisocyanate, tolylene diisocyanate or methanediphenylene diisocyanate.

7. The composition as claimed in claim 1, wherein A denotes the divalent radical derived from hexamethylene diisocyanate and wherein $R_1$ and $R_2$ denote a lauryl radical

10 or a mixture of radicals derived from tallow.

8. The composition as claimed in claim 1, wherein polyetherurethane has at least three urethane groups.

9. The composition as claimed in claim 8, wherein the polyetherurethane is selected from the groups consisting of:

Group I

The polyetherurethane of the following formula:

in which n is a number between 1 and 10, p, q, r and t, are equal to either 0 or 1, with at least one of q or r being equal to 1, and t being equal to zero when r is equal to 0, provided than when q is equal to 1, then either p, r and t are equal to 0, or p is equal to 0 and r and t are equal to 1, or t is equal to 0 and r and p are equal to 1, and when q is equal to 0, then r is equal to 1 and p and t are equal to 0;

Group II

The polyetherurethanes of the following formula II

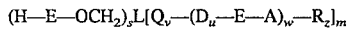

in which, m is an integer ranging from 2 to 4 and s is an integer ranging from 0 to 2, the sum of m and s ranging from 2 to 4, w is an integer ranging from 1 to 3, and each of u, v and z is, independently of each other, 0 or 1; L represents X, Y or —O—, X being a hydrophobic hydrocarbon radical containing at least one carbon atom, and Y a trivalent hydrophobic radical chosen from the following groups:

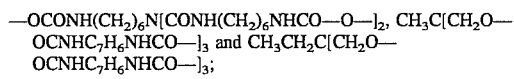

Q represents the group —CH$_2$C—, and D the group —CH$_2$O—, provided that, a) when L represents X, then u and w are each equal to 1, v and z are equal to 0, m is equal to not less than 2 and the sum of m and s is 4;

b) when L represents Y, then u, v and s are each equal to 0, m is equal to 3, w is 2 to 3 and z is 0 or 1; and c) when L represents —O—, then v and u are each equal to 1, w ranges from 1 to 3, m is equal to 2, and s and z are each equal to 0;

in each of the formulae for both of these groups, A and R represents a hydrophobic organic radical; B a hydrophobic divalent group of formula:

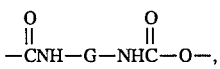

in which G is a divalent radical derived from an organic di- or triisocyanate all of whose isocyanate groups have reacted; and E represents a nonionic, divalent hydrophilic polyether group; and

Group III

The polyetherurethanes are obtained by reaction (a) of a polyfunctional reagent chosen from organic polyols having at least three hydroxyl groups, organic polyisocyanates having at least three isocyanate groups, and mixtures thereof;

(b) a difunctional reagent chosen from organic diols, organic diisocyanates, and mixtures thereof, the diol being present in the reaction mixture when the polyisocyanate is present and the diisocyanate being present when the polyol is present;

(c) a hydroxyl or amino monofunctional compound in a quantity sufficient to trap any isocyanate group which did not react during the reaction between (a) and (b), and to prevent coagulation of the reaction mixture; and, optionally, (d) an organic monoisocyanate for trapping the hydroxyl groups remaining after reaction between (a) and (b); wherein at least either the polyol or the diol contains at least one water-soluble polyether segment with a molecular weight of not less than 1500, the sum of the carbon atoms in the reagents containing isocyanate groups, hydroxyl groups and amino groups is not less than 20, and the average molecular weight of the components of the composition is about 10,000 to 200,000.

10. The composition of claim 9, wherein X contains one to four carbon atoms.

11. The composition as claimed in claim 1, wherein the nonionic surface-active agents of the family of alkyl polyglycosides are of the following formula:

$$R(C_5H_{10}O_5)_x\text{—H} \quad (II)$$

which corresponds to the following structural formula

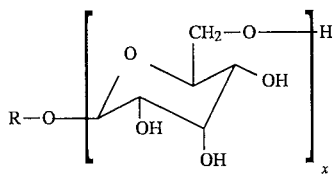

(III)

in which

R denotes an alkyl or alkenyl radical or a mixture of alkyl or alkenyl radicals containing a linear or branched $C_8$–$C_{24}$ chain;

x is a number between 1 and 15.

12. The composition as claimed in claim 1, wherein the polyglycerolated nonionic surface-active agents are selected from the group of polyhydroxypropyl ethers, consisting of:

(A) The compounds of the formula (IV):

$$RO[C_3H_5(OH)]_n H \quad (IV)$$

in which the group [$C_3H_5(OH)$] represents the following structures taken together or separately

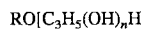 (IVa)

and

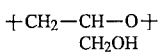 (IVb)

and

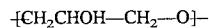 (IVc)

and R and n have one of the meanings below:

a) R represents a $C_{10}$–$C_{14}$ alkyl radical or a mixture of $C_{10}$–$C_{14}$ alkyl radicals and n is an integer or a decimal from 2 to 10, b) R represents a residue:

$$R_2\text{CONHCH}_2\text{—CH}_2\text{OCH}_2\text{—CH}_2\text{—} \quad (V)$$

where $R_2$ denotes a $C_{11}$–$C_{17}$ alkyl and/or alkenyl radical or a mixture of $C_{11}$–$C_{17}$ alkyl and/or alkenyl radicals and n denotes an integer or a decimal from 1 to 5, c) R represents a residue:

$$R_3\text{—CHOH—CH}_2\text{—} \quad (VI)$$

where $R_3$ denotes an aliphatic, cycloaliphatic or arylaliphatic $C_7$–$C_{21}$ radical and mixtures thereof, the aliphatic chains denoting in particular alkyl chains which contain from 1 to 6 ether, thioether and/or hydroxymethylene groups and n denotes an integer or decimal from 1 to 10;

(B) The compounds prepared by condensation, using acid catalysis, of 2 to 10 moles of glycidol per mole of alcohol or alpha-diol containing 10 to 14 carbon atoms, at a temperature of 50° to 120° C., the glycidol being slowly added to the alcohol or alpha-diol;

(C) The polyhydroxypropyl ether compounds prepared by polyaddition of glycerol monochlorohydrin to a polyhydroxylated organic compound in the presence of a strong base, with constant removal of water by distillation.

13. The composition of claim 12, wherein n is an integer or a decimal from 3 to 6.

14. The composition of claim 12, wherein n denotes an integer or a decimal from 1.5 to 4.

15. The composition of claim 12, wherein the compounds are prepared by condensation, using acid catalysis, of 2.5 to 6 moles of glycidol per mole of alcohol or alpha-diol.

16. The composition as claimed in claim 12, wherein the polyglycerolated nonionic surface-active agents are selected from the group of polyhydroxypropyl ethers consisting of:

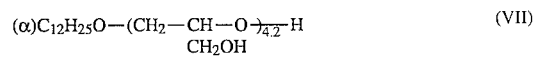 (VII)

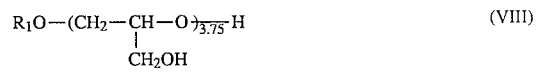 (VIII)

where $R_1$ denotes a mixture of $C_{10}H_{21}$ and $C_{12}H_{25}$ alkyl radicals;

(β) the compounds prepared by condensation, using alkaline catalysis, of 3.5 moles of glycidol with an alpha-diol having 12 carbon atoms;

(γ) the compounds of the formula:

$$R_2-CONH-CH_2-CH_2-O-CH_2-CH_2-O-(CH_2-CHOH-CH_2-O)_{3.5}-H \qquad (IX)$$

where $R_2$ denotes a mixture of radicals comprising the following alkyl and alkenyl radicals:
$C_{11}H_{23}$, $C_{13}H_{27}$, the radicals derived from fatty acids from copra and the radical derived from oleic acid;

(δ) the compounds obtained by condensation of 2.5 moles of glycerol monochlorohydrin with 1,2-dodecanediol in the presence of sodium hydroxide.

17. The composition as claimed in claim 1, which contains between 0.3 and 5% by weight relative to the total weight of the composition, of polyetherurethanes.

18. The composition as claimed in claim 1, which contains 3 to 50% by weight, relative to the total weight of the composition, of nonionic surface-active agents of the family of alkyl polyglycosides and/or polyglycerolated agents.

19. The composition of claim 18, which contains 5 to 30% by weight, relative to the total weight of the composition, of nonionic surface-active agents of the family of alkyl polyglycosides and/or polyglycerolated agents.

20. The composition as claimed in claim 1, wherein the cosmetically acceptable medium is an aqueous medium composed of water alone or of a mixture of water and a cosmetically acceptable organic solvent.

21. The composition as claimed in claim 1, which is provided in the form of a liquid which is thickened, a gel, emulsion, dilute alcoholic lotion, dispersion or aerosol foam.

22. A process for cosmetic treatment which comprises applying to the skin or the hair a cosmetically effective amount of the composition as claimed in claim 1.

23. A process for the cosmetic washing and treatment of hair which comprises in applying to wet or dry hair, an effective amount to wash the hair of the composition as described in claim 1 and wherein the hair is then rinsed with water.

24. The composition as claimed in claim 1, which further contains hydrocarbon containing oil, silicone waxes, silicone resins, silicone gums, silicone oils, acidifying agents, alkalinizing agents, preserving agents, suspending agents, emollients, sunscreen agents or perfumes.

25. The composition as claimed in claim 1, which further contains anionic surface-active agents, cationic surface-active agents, amphoteric surface-active agents, zwitterionic surface-active agents or non-ionic surface-active agents, other than those recited in claim 1.

26. The composition as claimed in claim 1, which further contains thickeners.

27. The composition as claimed in claim 1, which further contains anionic polymers, cationic polymers, non-ionic polymers or proteins, which are not surface-active agents.

* * * * *